United States Patent

Yamamoto et al.

[11] 4,008,330
[45] * Feb. 15, 1977

[54] METHOD FOR COMBATTING RODENTS AND RODENTICIDAL COMPOSITIONS

[75] Inventors: Hiroshi Yamamoto, Tokyo; Shoichi Kato, Ageo; Koji Ohgushi; Iwao Tokumitsu, both of Fukuoka, all of Japan

[73] Assignee: Nippon Kayaku Kabushiki Kaisha, Tokyo, Japan

[ * ] Notice: The portion of the term of this patent subsequent to July 1, 1992, has been disclaimed.

[22] Filed: Mar. 25, 1975

[21] Appl. No.: 561,980

Related U.S. Application Data

[62] Division of Ser. No. 286,058, Sept. 5, 1972, Pat. No. 3,892,864.

Foreign Application Priority Data

Sept. 13, 1971  Japan .............. 46-70390

[52] U.S. Cl. ............................................. 424/322
[51] Int. Cl.² .................... A01N 9/12; A01N 9/20
[58] Field of Search ............................ 424/322

[56] References Cited

UNITED STATES PATENTS 2,702,821  2/1955  Huebner et al. ............... 260/552
3,659,012  4/1972  Porter et al. .................. 424/322

OTHER PUBLICATIONS

Chem. Abst. 39, 2811(8), (1945), Dieke and Richter, Toxicity of Thiourea to Rats.
Chem. Abst. 41, 6662(g), (1947).

*Primary Examiner*—Albert T. Meyers
*Assistant Examiner*—D. W. Robinson
*Attorney, Agent, or Firm*—Russell & Nields

[57] ABSTRACT

This invention relates to a method for combatting rodents (especially animals which belong to Muridae) comprising applying a rodenticidally effective amount of a compound of general formula (1)

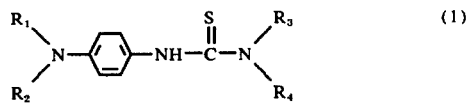

wherein $R_1$ is hydrogen or an alkyl group, $R_2$ is an alkyl group, $R_3$ is hydrogen or an alkyl group and $R_4$ is hydrogen, hydroxyl group, an alkyl group, a hydroxy-substituted alkyl group, benzoyl group or a halogen substituted phenyl group, or an acid addition salt thereof, and to rodenticidal compositions containing said compound or salt together with adjuvants.

5 Claims, No Drawings

METHOD FOR COMBATTING RODENTS AND RODENTICIDAL COMPOSITIONS

DETAILED EXPLANATION OF THE INVENTION

Heretofore, various rodenticides, in particular raticides have been developed. They are, however, linked with toxicity to men and cattle and their repelling property and any one of them are not satisfactory yet. For example, N-(1-naphthyl)thiourea, which is now widely used under the trade name "ANTU" have the disadvantage that, although of relatively low toxicity to human being, it will repel, once it is used, the rats in the applied area and prevent their access for bait over a considerable length of time.

We have made extensive research for those rodenticidal compounds eliminating these drawbacks and now found that compounds of the above-described general formula (1) have strong toxicity to rodents and relatively weak repelling property to maintain good rodents' access for bait, while having low toxicity to useful animals such as dogs, on which finding the present invention has been achieved.

Compounds used in the present invention may be prepared for example, by adding the corresponding aniline to a solution of benzoyl chloride and ammonium rhodanide in acetone, and boiling the mixture to condense the reactants. They may also be prepared by condensing phenyl isothiocyanate with the corresponding amine in the presence or absence of an appropriate solvent. Alternatively, compounds of general formula (1) wherein $R_3$ and $R_4$ are both hydrogen may be prepared by hydrolyzing a corresponding phenyl-3-benzoylthiourea with an aqueous sodium hydroxide solution. Acid addition salts include salts with hydrochloric acid, sulfuric acid and the like.

Compounds of general formula (1) used in the present invention may be applied by itself for combatting rodents by applying them to passages of rodents, but normally they are used together with adjuvants and a composition of the compound with adjuvants (for example carrier etc.) may be applied for combatting rodents by any suitable means, as by applying the composition to passages of rodents or by placing the composition as bait or poisonous drinking water where rodents are accessible to the bait or water.

As carrier, one may employ, for example, solid materials such as starch, kaolin clay, montmorillonite clay, diatomaceous earth and sugar, liquid materials such as xylenes, chlorobenzenes and the like aromatic hydrocarbons, methanol, ethanol and the like alcohols, ethanolamine and the like amines, aliphatic esters and water and favourite diets of rodents such as meats, meat extracts, rice, wheat flour, buckwheat flour, corn flour and the like cereals, sugar-cane, potato, seeds of sun flower, fish meal, fruits, vegetables and the like.

Compositions of the present invention may be used as rodenticidal compositions in form of powder, granules, pellets, solution, suspension, emulsion, paste and the like convenient form, optionally with the aid of an adjuvant such as carrier an emulsifying agent or a dispersing agent.

As emulsifying agents, one may employ, for example, nonionic and anionic emulsifying agents such as fatty acid ester or phosphoric acid ester of polyethylene glycol. As dispersing agents, one may employ, for example, calcium sulfonate.

The rodenticidal composition of the invention normally contains a compound of general formula (1) in concentrations of from 0.05% to 95%, preferably from 0.5 to 90% by weight.

Rodents which can be combatted according to the present invention include rats (Genus Rattus) and squirrels.

Representative examples of active compounds used in the present invention are given in Table 1.

Table 1

| Compound No. | Compound | Appearance | m.p. |
| --- | --- | --- | --- |
| 1 | 4-methylaminophenylthiourea | white needle-like crystals | 176 – 177° C |
| 2 | 4-dimethylaminophenylthiourea | white needle-like crystals | 194 – 196° C |
| 3 | 4-diethylaminophenyl-thiourea | white needle-like crystals | 168 – 169° C |
| 4 | 4-di-n-propylaminophenyl-thiourea | light yellow plate like crystals | 130 – 131° C |
| 5 | 4-di-n-butylaminophenyl-thiourea | white needle-like crystals | 107 – 108° C |
| 6 | 4-di-n-amylphenylthiourea | white plate-like crystals | 120 – 121° C |
| 7 | 4-dimethylaminophenyl-thiourea dihydrochloride | Gray crystals | 191 – 195° C (with decomposition) |
| 8 | N-hydroxy-N'-4-dimethylaminophenylthiourea | White crystals | 91 – 92° C |
| 9 | N-ethyl-N'-4-dimethylaminophenylthiourea | " | 142 – 143° C |
| 10 | N,N-diethyl-N'-4-dimethylaminophenylthiourea | " | 112 – 113° C |
| 11 | N-dodecyl-N'-4-dimethylaminophenylthiourea | " | 73 – 74° C |
| 12 | N-2-hydroxyethyl-N'-4-dimethylaminophenylthiourea | " | 174 – 175° C |
| 13 | N-4-chlorophenyl-N'-4-dimethylaminophenylthiourea | " | 196 – 197° C |
| 14 | N-benzoyl-N'-4-diethylaminophenylthiourea | Light yellow needle-like crystals | 130 – 132° C |

The following experiments illustrate that the active ingredient according to the present invention has excellent rodenticidal effects.

Experiment 1

Acute oral toxicity

A 3% starch solution was prepared, boiled and cooled and a given amount of a compound of general formula (1) was suspended therein. Test Norway rats were each orally given 2 ml of the suspension and then fed. After 5 days, inspection was made whether the animals survived or died. The results are shown in Table 2.

Table 2

| Compound No. | Test animals Body weight sex | Dose orally administered in mg/Kg | Raticidal effect Survival or death | Length of time until death |
| --- | --- | --- | --- | --- |
| 1 | 110 male | 300 | Died | within 1 day |
|   | 150 female | 200 | Survived |  |
| 2 | 95 female | 200 | Died | within 1 day |
|   | 150 male | 100 | " | " |
| 3 | 130 male | 200 | " | " |
|   | 100 femal | 100 | " | " |
| 4 | 120 male | 300 | " | " |
| 5 | 95 male | 200 | " | " |
|   | 140 male | 100 | Survived |  |
| 6 | 100 female | 200 | Died | within 1 day |
|   | 130 male | 100 | Survived |  |
| 7 | 190 male | 100 | Died | within 1 day |

Experiment 2

Toxicity test by libitium feeding technique

A single Norway rat was housed in each test cage (25 cm width × 35 cm length × 20 cm height) and was fed overnight by placing in the cage 10 g of a bait containing the active ingredient as prepared by the method described in Example 3 in a concentration of 1.0%, with said bait contained in a tall-skirted Petri dish. Inspection was made for the amount of the bait eaten (bait intake) and for the fatal effect of the active ingredient during 3 days. The results are shown in Table 3.

Table 3

| Compound No. | Test animals Species | Body weight sex in g | Bait intake in g | Active ingredient intake mg/Kg | Effect Survival or death | Length of time until death |
| --- | --- | --- | --- | --- | --- | --- |
| 1 | Norway rat | 285 male | 1.8 | 63.2 | died | within 1 day |
|   | " | 230 " | 0.5 | 21.7 | " | " |
|   | " | 335 " | 1.4 | 41.8 | " | " |
|   | " | 245 " | 1.9 | 77.6 | " | " |
| 2 | " | 195 " | 0.5 | 25.6 | " | " |
|   | " | 50 " | 0.5 | 320 | " | " |
|   | Roof rat | 125 " | 2.2 | 176 | " | within 2 days |
| 3 | Norway rat | 130 " | 3.1 | 238 | " | within 1 day |
|   | " | 220 " | 0.5 | 22.7 | " | within 2 days |
| 7 | " | 140 female | 0.5 | 36.7 | " | within 1 day |

Experiment 3

Toxicity test by powder-scattered surface walking technique

A wire netting cage of 30 cm in width, 90 cm in length and 60 cm in height having a nest box placed in it and another wire netting cage of 90 cm in width, 90 cm in length and 60 cm in height where water and diet were placed were brought into tight contact with each other, and connected through a 10 cm × 10 cm gateway through which a tunnel of 20 cm in width, 30 cm in length and 20 cm in height was provided. On the bottom surface of the tunnel was placed a vat of 20 cm in width and 25 cm in length scattered with a talc-based powder preparation containing the particular compound (Compound No. 2) in a concentration of 10% as prepared by the method described in Example 1 Test animals (1 male, 3 females, 4 animals in all, total body weight 790 g, mean body weight 198 g) were released in the cage. It is understood that the animals will walk on the powder-sprayed surface at every egress and ingress. Inspection was made for daily diet intake, the amount of the powder preparation consumed and the number of death. The results are shown in Table 4.

Table 4

|  | After 1 day | After 2 days |
| --- | --- | --- |
| Diet intake per animal | 1.25 g | 0 |
| The amount of the powder preparation consumed per animal | 0.73 g | 0 |
| Cumulative number of death | 3 animals (1 male, 2 females) | 4 animals |
| Cumulative fatality | 75 % | 100 % |

Experiment 4

Repelling property of baits

A single brown rat was housed in each wire netting test cage of 25 cm in width, 25 cm in length and 35 cm in height, fed overnight with 10 g non-poisonous feed as prepared by the similar method described in Example 3 contained in a tall-skirted Petri dish and further fed overnight with 10 g bait containing the active ingredient [Compound No. 2 or "ANTSU" (Trade name)] contained in a tall-skirted Petri dish. Feed or bait intake was examined in the respective cases. 20 Norway rats were used for each of the active compound containing baits.

The repelling property of the respective baits were evaluated by the relative repellency which is defined by the following equation:

$$\text{Relative repellency} = \frac{\text{Non-poisonous feed intake} - \text{bait intake}}{\text{bait intake}}$$

The results are shown in Table 5 in which the numerical values for relative repellency are averaged ones.

Table 5

| | Relative repellency | |
|---|---|---|
| Poison content in bait | 1 % | 0.5 % |
| Active ingredient | | |
| Compound No. 2 | 11.6 | 2.7 |
| ANTSU (known compound) | 31.4 | 7.8 |

Experiment 5

Toxicity to dogs

Cream bun was cut into pieces as large as hen's eggs and the pieces were provided in the central portion thereof with a hollow. To this hollow was added milk together with Compound No. 2 to embed the latter in the hollow. The cream bun pieces thus treated were given to dogs by hand. The results are shown in Table 6.

Table 6

| Dose administered in mg/kg | Test dogs | | | | Survival or Death |
|---|---|---|---|---|---|
| | Species | Color of fur | Body weight Sex | Age in years | |
| 100 | Mongrel | hight brown | 10 kg Femal | 2 | Survived |
| 400 | " | Black | 7 kg " | 1 | Survived |
| 600 | " | Brown | 12 kg male | 4 | Survived |

Experiment 6

A single Norway rat was housed in each of test cages of 25 cm in width, 35 cm in length and 20 cm in height each, and fed overnight with 10 bait as prepared by the method described in Example 3, containing the stated compound in a concentration of 1.0%, while keeping the bait in a tall-skirted Petri dish. The bait intake and the fatal effect within 5 days were examined. The results are shown in Table 7.

Table 7

| Compound No. | Test animals | | | Bait | Effect | |
|---|---|---|---|---|---|---|
| | Body weight in g | Sex | Intake in g | Active ingredient intake mg/Kg | Survival or death | Length of time until death |
| 8 | 170 | Male | 1.6 | 940 | Died | within 4 days |
| | 200 | " | 2.3 | 115 | " | within 2 days |
| 9 | 240 | " | 0.1 | 16.5 | " | within 3 days |
| | 205 | " | 0.1 | 4.9 | " | within 4 days |
| 10 | 115 | " | 4.8 | 417 | " | within 2 days |
| | 185 | Female | 0.3 | 16.2 | " | within 4 days |
| 11 | 255 | Male | 3.8 | 419 | " | within 2 days |
| | 220 | Female | 2.5 | 117 | Survived | |
| 12 | 225 | Male | 2.3 | 102 | Died | within 2 days |
| | 185 | Female | 1.3 | 70.2 | " | within 4 days |
| 13 | 215 | Male | 1.8 | 83.7 | " | within 3 days |
| | 190 | " | 4.4 | 232 | Survived | |
| 14 | 240 | " | 2.1 | 87.5 | Died | within 2 days |
| | 165 | Female | 0.8 | 48.5 | " | within 2 days |

The present invention will be further explained with some of the compounds according to the present invention. It is understood, however, that the contents of the active ingredients and additives may vary over a wide range. In these examples, all percentages (%) are by weight.

| Compound No. 1 | 10 % |
|---|---|
| talc | 90 % | are admixed to give a powder preparation.

| Compound No. 6 | 10 % |
|---|---|
| Starch | 90 % | are admixed and 10 parts of the admixture is sprinkled on 100 parts of sweat-cane, potato, bread or fried bean-curd to give a bait.

| Compound No. 2 | 1 % |
|---|---|
| corn flour | 10 % |
| buckwheat flour | 10 % |
| wheat flour | 65 % |
| rice bran | 10 % |
| fish meal | 4 % | are admixed and 100 parts of the admixture is kneaded with 20 parts of water added and formed into cylindrical granules, which are then dried to give a bait.

| Compound No. 8 | 10 % |
|---|---|
| Starch | 45 % |
| molasses | 25 % |

-continued

| | |
|---|---|
| meat extracts | 5 % |
| sesame oil | 15 % | are admixed and 10 parts of the admixture sprinkled on 100 parts of sweat-cane, potato, bread, fried beancurd or the like to give a bait.

| | |
|---|---|
| Compound No. 11 | 1 % |
| soluble starch | 20.9 % |
| sugar | 5 % |
| sodium benzoate | 0.1 % |
| water | 73 % | are admixed to give an aqueous bait.

| | |
|---|---|
| Compound No. 14 | 1 % |
| wheat flour | 69 % |
| sugar | 5 % |
| sesame oil | 5 % |
| water | 20 % | are kneaded and formed into doughboys each weighing 0.5 g to give a bait.

EXAMPLE 7

Powdered Compound No. 8 is applied as such to a passage of rats.

EXAMPLE 8

Powder of Compound No. 8 is applied to sweet potato cut into cubes 3 mm cube in a manner such that the content of said compound may become 1 %, to give a bait.

EXAMPLE 9

Grains of wheat are dipped in a 10 % aqueous sugar solution and powder of Compound No. 2 sprinkled on the solution to give a bait.

EXAMPLE 10

20 parts of water is added to 100 parts of corn flour and kneaded therewith and 10 parts of powder of Compound No. 3 is admixed with the dough to give a bait.

EXAMPLE 11

1 part of powder of Compound No. 6 is suspended in 100 parts of an edible oil to give a bait or a sprinkling composition.

EXAMPLE 12

Powder of Compound No. 8 is sprinkled on bread impregnated with a 10 % aqueous sugar solutions give a diet.

What is claimed is:

1. A method for combatting rodents comprising the step of applying to a surface which rodents may be expected to contact a rodenticidal powder other than a feed bait comprising 99.5–10% by weight of a suitable adjuvant and a rodenticidally effective amount of 0.5–90% by weight of a compound of the formula.

$$\begin{array}{c} R_1 \\ \diagdown \\ R_2 \end{array} N - \bigcirc - NH - \overset{S}{\underset{\|}{C}} - N \begin{array}{c} R_3 \\ \diagup \\ R_4 \end{array}$$

wherein $R_1$ is hydrogen or alkyl of 1 to 5 carbons, $R_2$ is alkyl of 1 to 5 carbons, $R_3$ is hydrogen or alkyl of 1 to 2 carbons, and $R_4$ is hydrogen or alkyl of 1 to 12 carbons, or a hydrochloric acid salt thereof.

2. The method as claimed in claim 1, wherein said compound is $$\begin{array}{c} R_1 \\ \diagdown \\ R_2 \end{array} N - \bigcirc - NH - \overset{S}{\underset{\|}{C}} - NH_2$$

wherein $R_1$ is hydrogen or alkyl of 1 to 5 carbons and $R_2$ is alkyl of 1 to 5 carbons or a hydrochloric acid salt thereof.

3. The method as claimed in claim 1, wherein said rodents are rats (Genus Rattus).

4. A rodenticidal powder other than a feed bait comprising 99.5 – 10% by weight of a suitable adjuvant and a rodenticidally effective amount of 0.5 – 90% by weight of a compound of the formula $$\begin{array}{c} R_1 \\ \diagdown \\ R_2 \end{array} N - \bigcirc - NH - \overset{S}{\underset{\|}{C}} - NH_2$$

wherein $R_1$ is hydrogen or alkyl of 1 to 5 carbons and $R_2$ is alkyl of 1 to 5 carbons.

5. The composition for combatting rodents as claimed in claim 4, wherein said rodents belong to Muridae.

* * * * *